United States Patent [19]
Doi et al.

[11] Patent Number: 5,331,407
[45] Date of Patent: Jul. 19, 1994

[54] METHOD AND APPARATUS FOR DETECTING A CIRCUIT PATTERN

[75] Inventors: Hideaki Doi, Oota; Yasuhiko Hara, Machida; Koichi Karasaki, Hadano, all of Japan

[73] Assignee: Hitaci, Ltd., Tokyo, Japan

[21] Appl. No.: 845,723

[22] Filed: Mar. 4, 1992

[30] Foreign Application Priority Data

Mar. 4, 1991 [JP] Japan .................................. 3-037142

[51] Int. Cl.$^5$ ........................ G01N 21/88; G01B 7/00
[52] U.S. Cl. .................................... 356/394; 356/237; 382/8
[58] Field of Search ................ 356/394, 237; 382/8

[56] References Cited

U.S. PATENT DOCUMENTS

| | | | |
|---|---|---|---|
| 4,012,147 | 3/1977 | Walrafen | 356/301 |
| 4,559,603 | 12/1985 | Yoshikawa et al. | 356/394 |
| 4,628,531 | 12/1986 | Okamoto et al. | 356/394 |
| 4,993,834 | 2/1991 | Carlhoff et al. | 356/328 |

Primary Examiner—F. L. Evans
Attorney, Agent, or Firm—Antonelli, Terry, Stout & Kraus

[57] ABSTRACT

A method and apparatus for detecting a circuit pattern comprise a stage for mounting an object under inspection having a circuit pattern to be detected, means of generating a signal in response to the amount of movement of the stage, a detection optical system for detecting the circuit pattern, an opto-electric transducer which receives the image of the pattern provided by the detection optical system and transforms the image into an image signal, means of calculating the amount of expansion or contraction of the object by detecting the distance between specific patterns on the object, and drive control means which produces a clock signal for the opto-electric transducer based on the stage movement signal provided by the signal generation means and varies the clock signal so as to vary the dimension of the detected image arbitrarily.

21 Claims, 6 Drawing Sheets

METHOD AND APPARATUS FOR DETECTING A CIRCUIT PATTERN

BACKGROUND OF THE INVENTION

The present invention relates to a method and apparatus for detecting defects of a circuit pattern such as a wiring pattern on a printed wiring board or a thin film wiring pattern on a ceramic substrate, and particularly to a method and apparatus for detecting defects of pattern by compensating the expansion or contraction and the inclination of an object to be inspected.

A known method for inspecting a circuit pattern such as a wiring pattern on a printed circuit board is designed to compare a circuit pattern under test with a reference pattern derived from design data or the like, thereby detecting defects of the circuit pattern. For the comparison-based inspection, it is indispensable to align the two circuit patterns accurately. However, setting a circuit board under test to the inspection apparatus is vulnerable to the alignment error and the displacement caused by the expansion or contraction of the circuit board, and the following methods and apparatus are proposed to overcome the problem. An example described in Japanese Patent Unexamined Publication No. 61-151709 is a comparison-based inspection method which memorized a circuit pattern in a memory and reads out the circuit pattern so that the displacement is minimal. Another example described in Japanese Patent Unexamined Publication No. 2-159545 is an alignment method which modifies the evaluated dimension of a detected circuit pattern by varying the timing of pattern introduction.

The above-mentioned prior art described in the patent publication No. 61-151709 cannot recognize the displacement between the two circuit patterns if the circuit board includes an area where no circuit pattern exists, and it is incapable of aligning circuit patterns if the displacement is in excess of the preset alignment range. The resolution of alignment is limited to the accuracy of evaluation of the pattern dimension.

The above-mentioned prior art described in the patent publication No. 2-159545 is capable of aligning the circuit patterns at a resolution finer than the evaluated dimension. However, it necessitates stage pulses with a 1% accuracy of evaluated dimension for compensating a 1% displacement, for example, and it is difficult to apply the technique to the inspection of a circuit pattern with a small evaluated dimension.

SUMMARY OF THE INVENTION

The present invention is intended to overcome the foregoing prior art deficiencies, and its prime object is to provide a method and apparatus for inspecting a circuit pattern based on the comparison through the enhancement of the pattern alignment accuracy.

Another object of the present invention is to provide a method and apparatus for circuit pattern detection which can be applied to the inspection of a circuit pattern with a small evaluated dimension.

Still another object of the present invention is to provide a pattern generator which can generate a reference pattern efficiently.

The present invention resides in a circuit pattern detecting apparatus which comprises an x/y stage for mounting an object having a circuit pattern to be detected, a device for generating a signal which represents the amount of movement of the stage, and an opto-electric transducer and associated optical system for detecting the circuit pattern, wherein a transducer clock signal is produced from the stage movement signal and the clock signal is varied so that the dimension of pixel of the detected pattern is varied arbitrarily.

The present invention resides in a circuit pattern inspecting apparatus which comprises the above-mentioned circuit pattern detecting apparatus that is provided with a device for generating a reference pattern and operates to detect defects of a circuit pattern based on the comparison with the reference pattern, wherein the distance between specific circuit patterns on the object under test is measured and it is compared with the corresponding distance on the reference pattern thereby to evaluate the amount of expansion or contraction of the object, and the above-mentioned transducer clock signal is varied depending on the object variation value for the alignment of the object circuit pattern and the reference pattern.

The present invention resides in a circuit pattern detecting apparatus which comprises a device for generating pulses in response to the amount of movement of the above-mentioned x/y stage, wherein the above-mentioned transducer clock signal is generated in response to a certain count value of the stage movement pulses and the pulse count value is varied arbitrarily.

The present invention resides in the above-mentioned circuit pattern inspecting apparatus which operates to align a circuit pattern under test and the reference pattern by detecting the object circuit pattern through the relative step movement between the object and a sensor, with the amount of step movement being set so that detection areas overlap and with the amount of step movement being varied for the alignment of the object circuit pattern and the reference pattern.

The present invention resides in a reference pattern generator which comprises a means of generating a pattern from design information in which the dimension of a pixel is magnified by n fold (n is a positive number) and storing the pattern, and a means of producing a reference pattern by reading out the pattern m times (m is a positive integer).

The present invention resides in a reference pattern generator which comprises a line memory for storing n scanning lines and produces a 2-dimensional reference pattern having an intended dimension of a pixel.

The present invention resides in a circuit pattern inspecting apparatus which comprises a plurality of opto-electric transducers and associated optical systems for detecting a circuit pattern.

The present invention resides in a circuit pattern detecting apparatus which comprises an illumination system, a detecting optical system and a sensor, wherein a means of conducting the illumination light based on optical fiber is provided, with the outlet of the optical fiber being positioned so as to correspond to and illuminate the detection area of the sensor.

In detecting defects of a circuit pattern under test based on the comparison with the reference pattern derived from design data or the like, when the substrate of a reference pattern (with a length of L) is divided into N segments (with a pixel dimension of $\Delta$), the object substrate (with a length of L') is also divided into N segments so that the same position of both substrates are compared. It is assumed that the object mount stage is moved continuously in the first direction and it is moved in steps in the second direction which intersects the first direction. The object circuit pattern is read in response to the movement of the object, and the moving distance of the stage represents the pixel dimension Δ' of the object pattern in the first direction. For the pixel dimension Δ' with a value of x when the substrate has no expansion nor contraction, the number of division N cannot be retained constant when the Δ' is fixed to x in case the substrate has an expansion or contraction. On this account, the detection pixel size Δ' is switched between the normal value x and altered value x' depending on the value of expansion or contraction. The frequency of switching is calculated by detecting the corner mark position prior to the commencement of inspection. For the second direction, the pitch of step movement Xp is varied to match the expansion or contraction of the substrate. The value of alteration is determined by detecting the corner mark position before the commencement of inspection.

Based on the foregoing arrangement, the value of expansion or contraction of the object circuit pattern is compensated at the time of pattern reading. According to the present invention, it becomes possible to compare the object circuit pattern with the reference pattern through the compensation of the expansion and contraction of the object pattern, whereby accurate component inspection can be accomplished.

DESCRIPTION OF THE PREFERRED EMBODIMENTS

An embodiment of this invention will be described with reference to the drawings.

Figure 1:
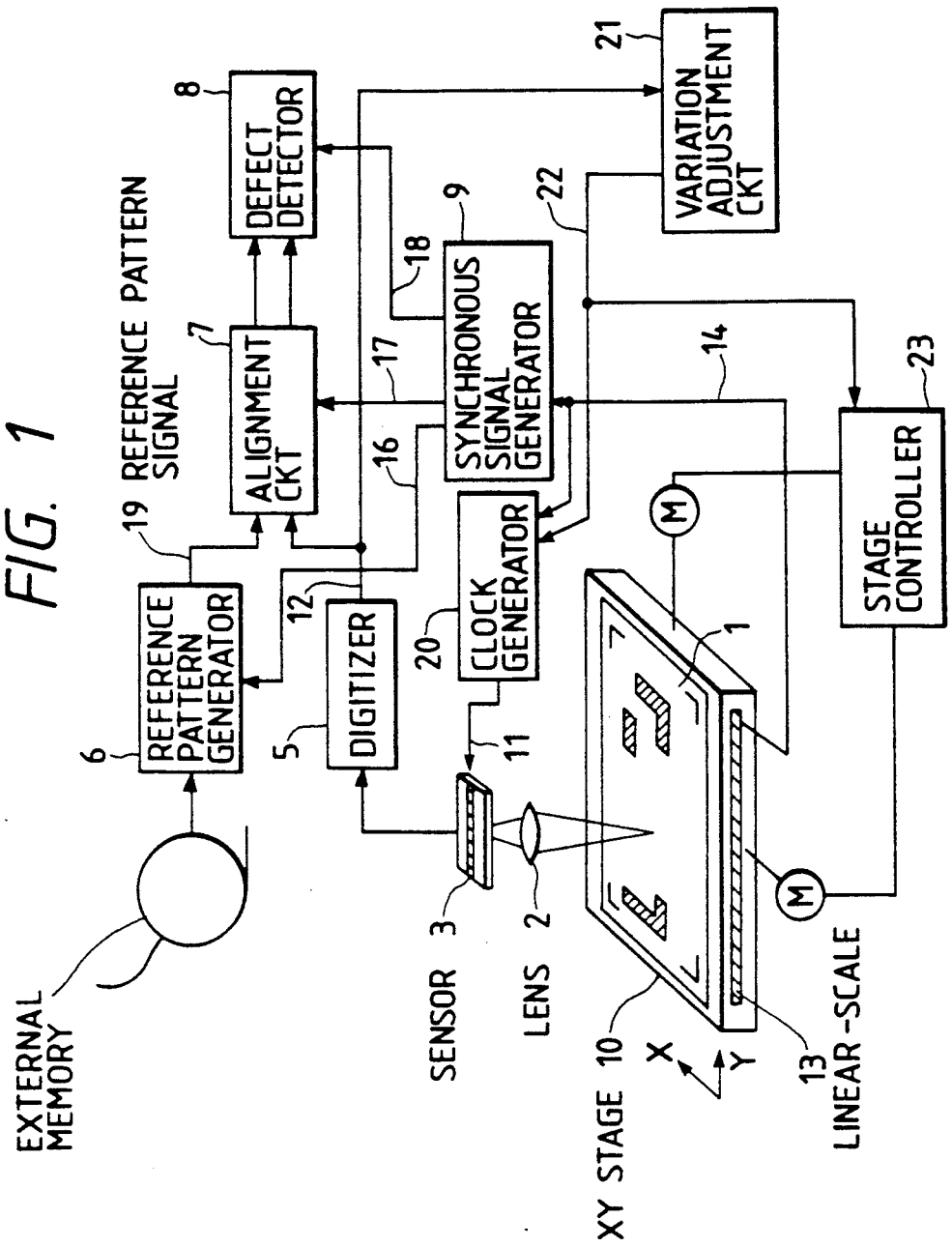
FIG. 1 is a block diagram showing the circuit pattern inspection apparatus based on an embodiment of the present invention.

FIG. 1 is a block diagram showing the circuit pattern inspection apparatus based on an embodiment of this invention. An object 1, such as a printed circuit board, to be inspected is imaged on a sensor 3 through a lens 2. The sensor 3 implements the opto-electric transformation for the image in synchronism with clock pulses 11, and the resulting image information of the object 1 is converted into a binary image signal 12 by means of a threshold circuit 5. The object 1 is placed on an x/y stage 10 which can be moved in steps in the x direction and can be moved continuously in the y direction. The x/y stage 10 has the attachment of a linear scale 13 as shown in FIG. 1, which produces a number of stage pulses 14 in proportion to the moving distance of the stage 10, and the pulses are fed to a synchronous (sync) signal generator 9. The sync signal generator 9 produces inspection position signals 16-18 from the stage pulses 14 in response to the movement of the x/y stage 10, i.e., the movement of the object 1.

An external memory 4 stores a record of design information pertinent to the manufacturing of the object 1. A reference pattern generator 6 produces a reference pattern signal 19, which is used for the comparison-based inspection, based on the design information by being timed to the inspection position signal 16. A clock generator 20 produces clock pulses 11 from stage pulses 14.

An alignment circuit 7 implements the electrical alignment between the reference pattern signal 19 and binary image signal 12 in synchronism with the inspection position signal 17, and delivers the result to a defect detector 8. The defect detector 8 detects defects of the circuit pattern under inspection based on the comparison with the reference pattern.

A variation adjustment circuit 21 evaluates the amount of expansion or contraction of the object based on the method explained later, and the resulting variation adjustment data 22 is used for controlling the operation of the clock generator 20 and stage controller 23. The alignment circuit 7 performs the electrical alignment of data in the memory, and it is a technique known as "template pattern matching" based on the reference pattern. This function is employed with the intention of correcting a local displacement. The inspection position signals 17 and 18 are used to mask off certain regions of the object (turning positions of the stage, etc. ).

Figure 2:
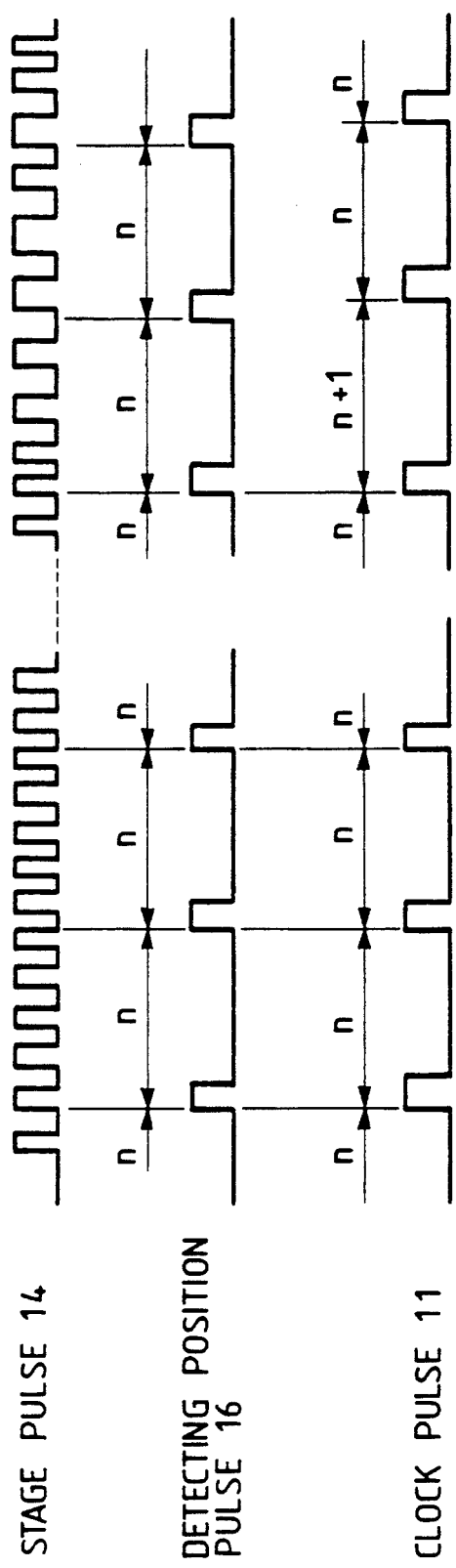
FIG. 2 is a timing chart used to explain the alignment method based on this invention.

FIG. 2 shows the relation among the stage pulse 14 produced by the linear scale 13, the inspection position signal 16 provided by the sync signal generator 9 and the clock pulse 11 provided by the clock generator 20. Each stage pulse 14 is generated for a certain moving distance d of the x/y stage 10, and the sync signal generator 9 produces the inspection position signal 16 at every n count of pulses, i.e., in every n·d distance of movement. Accordingly, the reference pattern generator 6 delivers the reference pattern 19 at a resolution of n·d in response to the signal 16.

The clock generator 20 counts the stage pulses 14 to produce the clock pulse 11, and it controls (varies) the clock pulse 11 in accordance with the variation adjustment data 22 from the variation adjustment circuit 21 so that the count value is normally n and occasionally n' (at a frequency of f). Namely, clock generator 20 controls the clock pulse 11 to vary the timing of imaging of the sensor 3, and consequently the inspection circuit pattern has its resolution varied between n·d normally and n'·d occasionally. The frequency of having the resolution n'·d is determined by the variation adjustment data 22 provided by the variation adjustment circuit 21. The highest accuracy is attained when n' is set equal to n±1.

Figure 3:
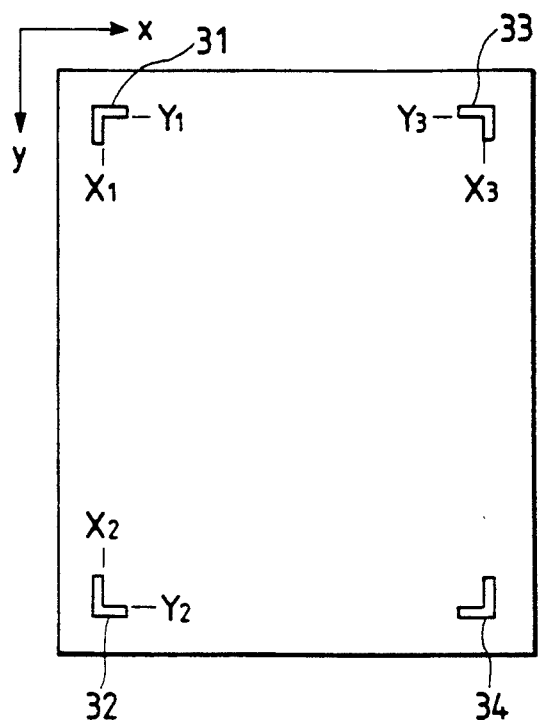
FIG. 3 is a diagram showing an example of objects to be inspected pertinent to this invention.

The operation of the variation adjustment circuit 21 will be explained with reference to FIG. 3. Before the commencement of inspection, the variation adjustment circuit 21 detects the positions of alignment marks 31 and 32 on the object 1 based on the binary signal provided by the sensor 3 and threshold circuit 5. It is assumed that positions of the alignment marks 31 and 32 are detected as y-axis coordinate values of $Y_1$ and $Y_2$. The reference pattern also has alignment marks 31 and 32 with y-axis coordinate values $Yo_1$ and $Yo_2$, which are preset in the variation adjustment circuit 21. The variation adjustment circuit 21 calculates the value of variation δy as follows.

$$\delta y = (Y_2 - Y_1) - (Yo_2 - Yo_1) \qquad (1)$$

The number of generation t of the stage pulse 14 between the alignment marks 31 and 32 (across the scanning range in the y direction) in the normal state (without expansion and contraction) is given by the following equation and it is preset in the variation adjustment circuit 21.

$$t = (Y_{o2} - Y_{o1})/(n \cdot d) \qquad (2)$$

The variation adjustment circuit 21 calculates the frequency f of occurrence of $n' = n \pm 1$ from the following equation (3), and delivers the value to the clock generator 20.

$$f = t/\delta y \qquad (3)$$

The clock generator 20 produces a clock pulse 11 at every n counts (n is arbitrary) of the stage pulses 14, and it counts the stage pulses 14 until $n' = n \pm 1$ once every f-th generation of the clock pulse 11. Addition or subtraction of $n \pm 1$ is determined corresponding to the positive or negative polarity of $\delta y$. Although the special count value is $n' = n \pm 1$ in the above explanation, it can be chosen arbitrarily.

Figure 4:
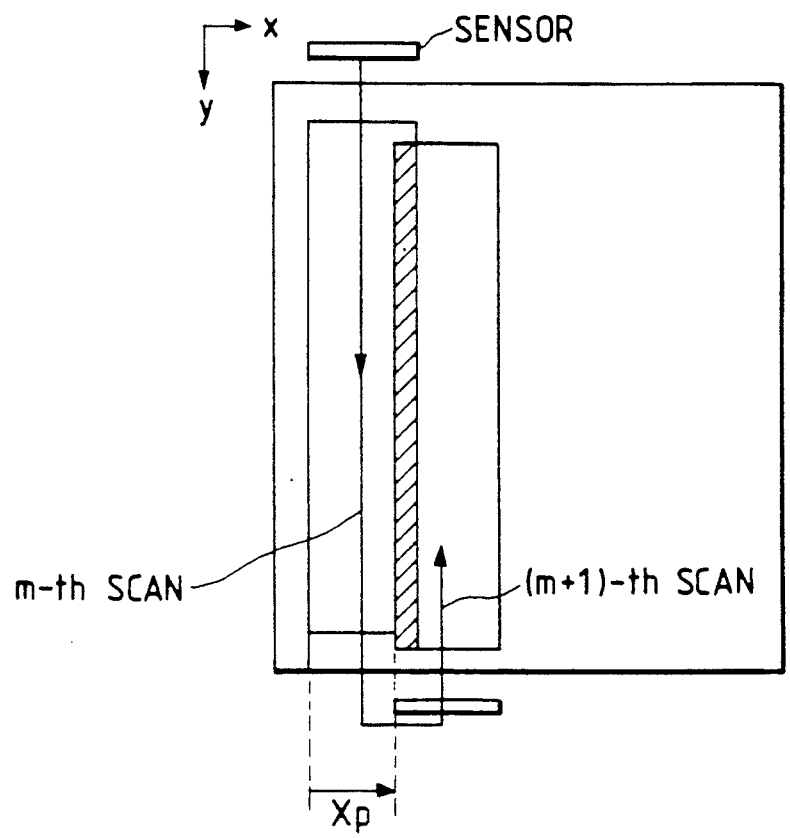
FIG. 4 is a diagram used to explain the alignment method based on this invention.

Next, the method of variation compensation in the x direction will be explained with reference to FIG. 4. The stage controller 23 controls the x/y stage 10 so that elongated inspection areas of consecutive scanning operations partially overlap as shown in FIG. 4, thereby preventing any portion from being missed out. The adjoining inspection area is shifted by the step feed value Xp of the sensor.

Before the commencement of inspection, the variation adjustment circuit 21 detects the positions of alignment marks 31 and 33 on the object 1 based on the binary signal provided by the sensor 3 and threshold circuit 5. It is assumed that positions of the alignment marks 31 and 33 are detected as x-axis coordinate values of $X_1$ and $X_3$. The reference pattern also has preset x-axis coordinate values $X_{o1}$ and $X_{o3}$ which are compared to the $X_1$ and $X_3$. The variation adjustment circuit 21 calculates the value of variation $\delta x$ as follows.

$$\delta x = (X_3 - X_1) - (X_{o3} - X_{o1}) \qquad (4)$$

It is assumed that there are m elongated inspection areas between the alignment marks 31 and 33. In order to compensate the variation value $\delta x$, the variation adjustment circuit 21 calculates a value Xp' based on the following equation (5), and delivers the result to the stage controller 23.

$$Xp' = \delta x/(m-1) + Xp \qquad (5)$$

The stage controller 23 operates to step-feed the x/y stage 10 by the value Xp' in place of the Xp. The overlap value preset in the stage controller 23 is selected to be greater than the maximum value of $(Xp' - Xp)$ so that it absorbs an increase or decrease of Xp' with respect to Xp.

Although the above explanation is the case of individual variation adjustments for y and x directions, when the object has an inclination, the synchronism between the reference pattern and object circuit pattern is offset in the y direction by using the y-axis coordinate value $Y_1$ and $Y_3$ of the alignment marks 31 and 33 as the starting signal supplied from the variation adjustment circuit 21 to the clock generator 20. Namely, the alignment mark 33 is distant from the alignment mark 31 by $Y_3 - Y_1$, and starting of the reference pattern and object circuit pattern is shifted for elongated inspection areas of m in number as follows.

$$Y_s = (Y_3 - Y_1)/m \qquad (6)$$

This adjustment can be attained by varying the timing of generation of the clock pulse 11 and inspection position signal 16 to match the value of Ys.

The foregoing embodiment is capable of aligning the object circuit pattern and reference pattern accurately on a real-time basis, and a reliable inspection apparatus can be accomplished. The alignment accuracy is high since it does not directly depend on the resolution of the stage pulse.

Figure 7:
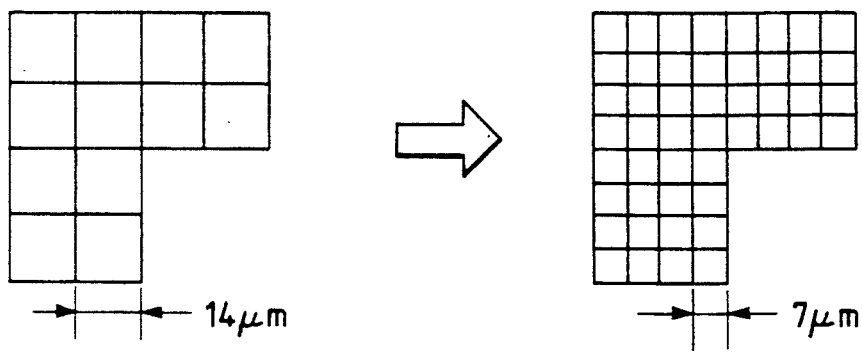
FIG. 7 is a diagram used to explain the reference pattern generation method based on this invention.
Figure 8:
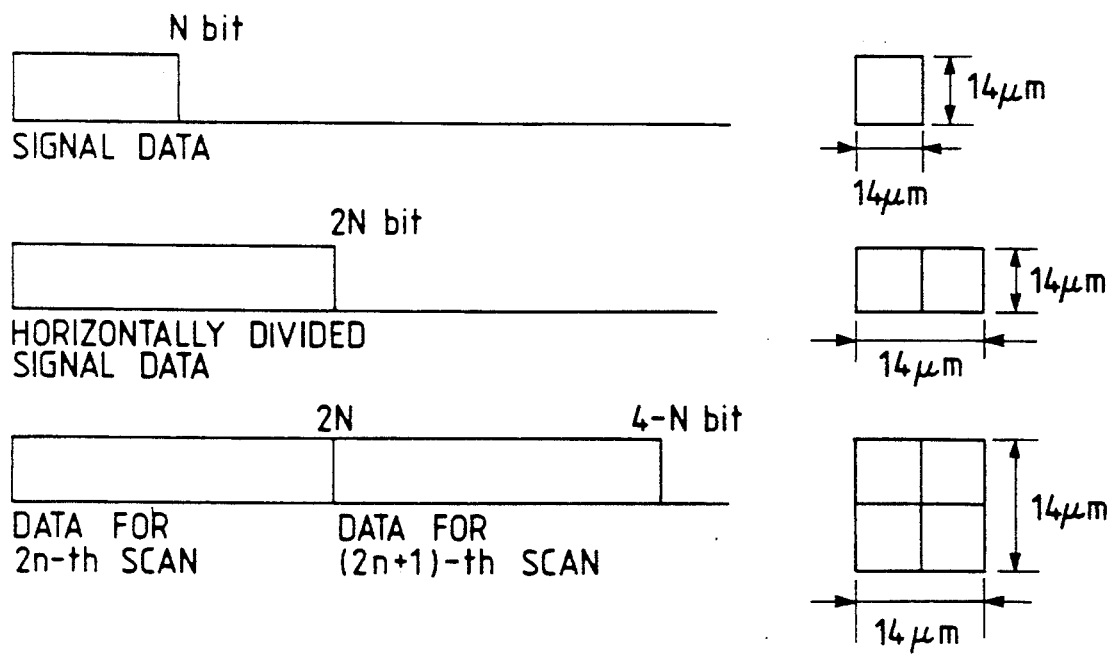
FIG. 8 is a diagram used to explain the reference pattern generation method based on this invention.

Next, an embodiment of the reference pattern generator will be explained. Shown in FIG. 7 is an example of pixel division, in which a reference pattern based on 14 $\mu$m pixels is used for inspection by halving the pixel size to 7 $\mu$m. A pixel is split into two in the lateral direction with reference to the reference pattern signal 19 by means of a latch circuit or the like (not shown), as shown in FIG. 8. The transfer clock supplied to the latch circuit has a frequency twice that of the reference pattern signal 19. The resulting pixel data is fed to a line memory (not shown), and then the same line is read out twice at a clock frequency twice the transfer frequency, i.e., four times the reference pattern signal frequency. According to this embodiment, the reference pattern generator 6 operates as slow as ¼ of the inspection speed. Although this embodiment is the case of reference pattern pixel size which is twice the inspection pixel size, the factor k of pixel size multiplication is arbitrary.

Figure 5:
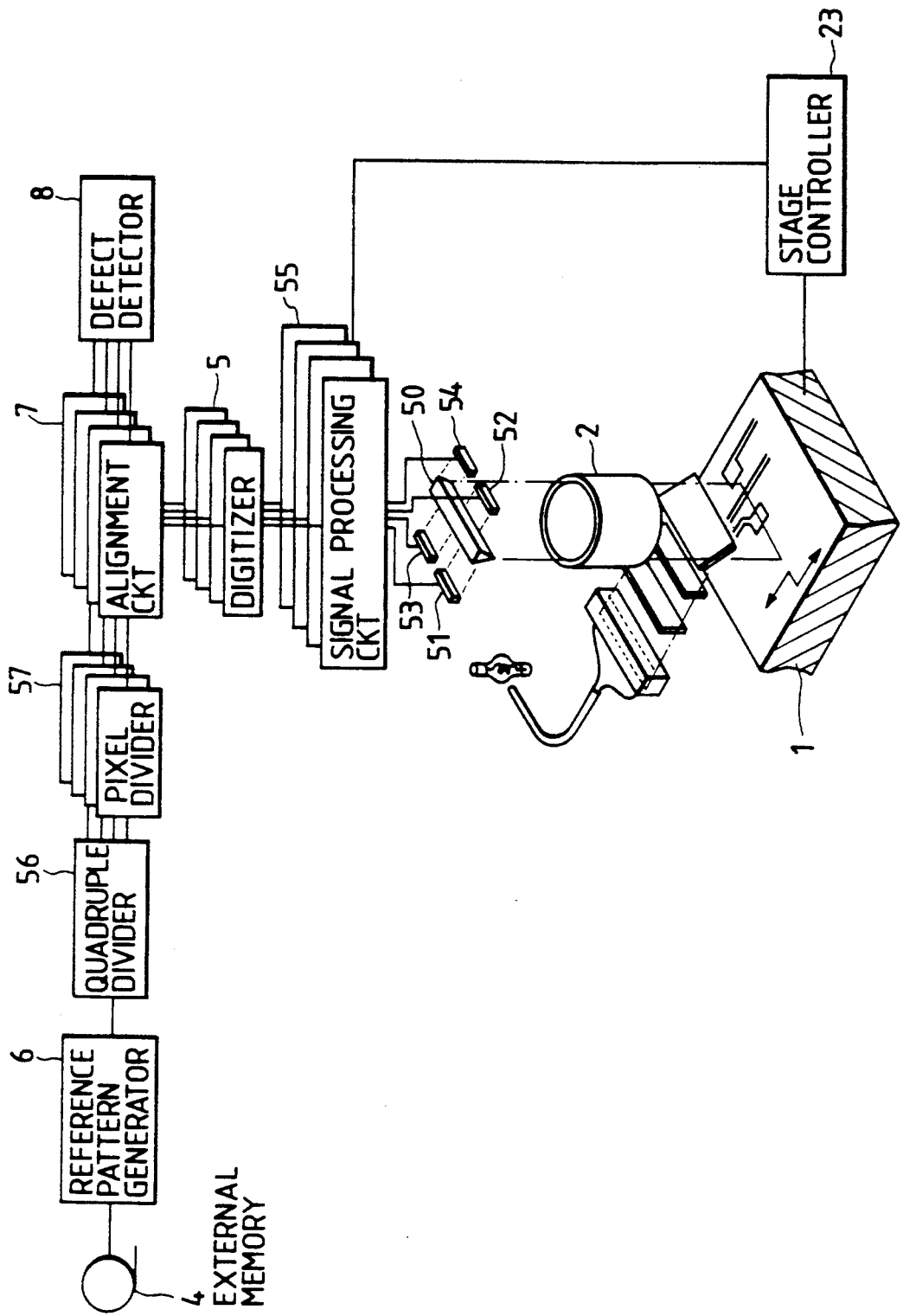
FIG. 5 is a diagram showing the arrangement of the circuit pattern inspection apparatus based on an embodiment of this invention.
Figure 6:
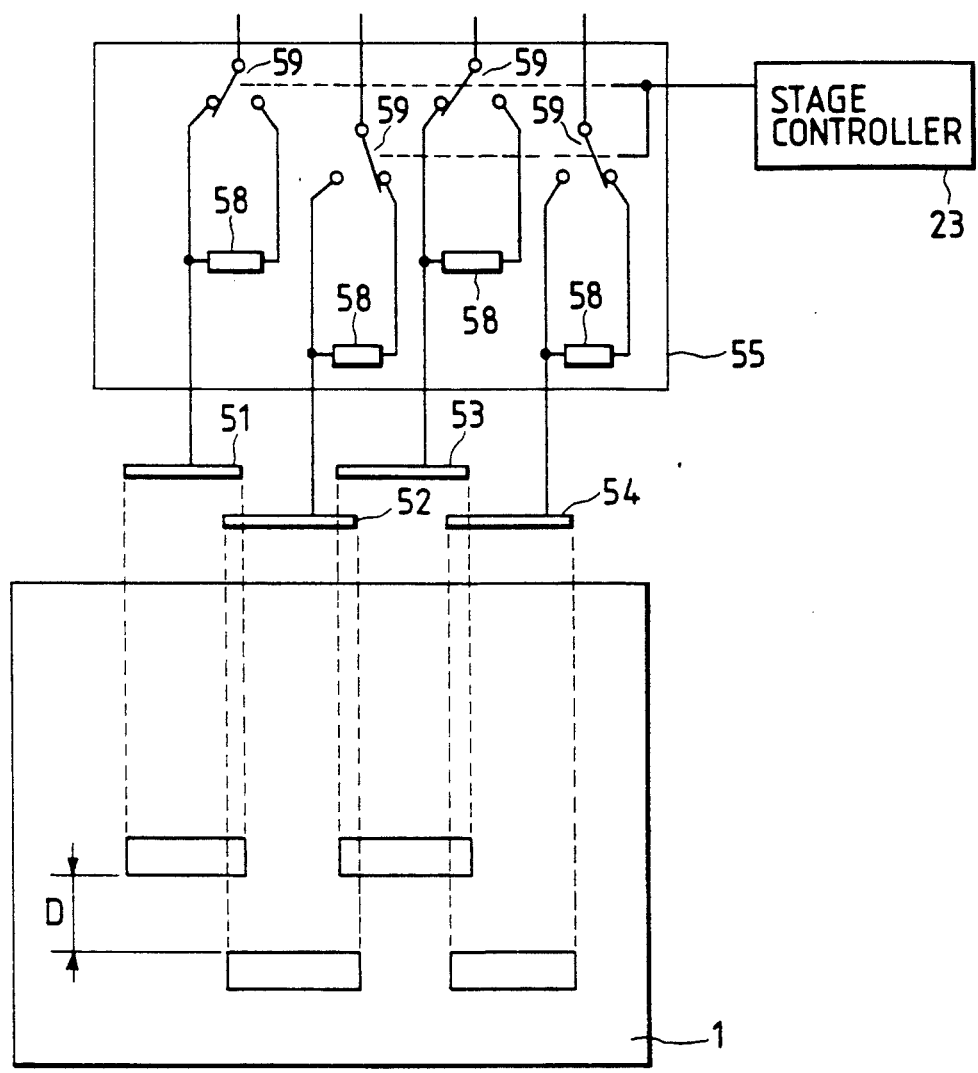
FIG. 6 is a block diagram showing the signal processing method based on an embodiment of this invention.

In the arrangement shown in FIG. 5, a prism 50 is used to distribute the detected signal to four linear sensors 51–54. The linear sensors 51–54 have individual detection regions on the object 1 as shown in FIG. 6, and a signal processing circuit 55 delays the signal by the amount corresponding to the distance D between sensors by means of line memories 58. It is necessary to switch the amount of delay of the line memories 58 for the combination of sensors 51 and 53 or sensors 52 and 54 by means of a switch 59 depending on the moving direction of the x/y stage 10. The signal of stage moving direction is obtained from the stage controller 23, for example. The sensors 51–64 are enclosed in relatively large packages and it is generally difficult to detect the whole area continuously, whereas according to this embodiment a plurality of sensors can be used as a single large sensor in a practical sense. A quadruple divider 56 is to divide the reference pattern signal 19 for individual sensors, and the divided signal are fed to the pixel divider 57 (made up of latch circuits, line memories, etc.). A linear illumination produced by use of an optical fiber is provided for the linear inspection area as shown in FIG. 5. This illumination system utilizing the optical fiber converts a circular illumination beam into the shape of the detection area and therefore it operates efficiently. That is, the illumination system has an outlet providing a shape corresponding to the rectangular shape of the detection area of the sensor.

According to the present invention, as described above, it becomes possible to compare the object circuit pattern with the reference pattern by compensating the expansion or contraction of the object, whereby accurate circuit pattern inspection can be accomplished.

What is claimed is:

1. An apparatus for detecting a circuit pattern comprising: a stage for mounting an object under inspection having a circuit pattern to be detected; means of generating a signal in response to the amount of movement of said stage; a detection optical system for detecting the circuit pattern; an opto-electric transducer which receives the image of the pattern provided by said detection optical system and transforms the image into an image signal; and drive control means which produces a clock signal for said opto-electric transducer based on the stage movement signal provided by said signal generation means and varies the clock signal so as to vary the dimension of the detected image arbitrarily.

2. A circuit pattern detection apparatus according to claim 1 further comprising: means of generating a reference pattern; means of aligning relatively the reference pattern provided by said reference pattern generation means and the image signal provided by said opto-electric transducer; and a judgement means which compares the reference pattern and the detected image signal aligned by said alignment means thereby to detect a defect.

3. An apparatus for detecting a circuit pattern according to claim 1, further comprising means of conducting an illumination light, said conducting means having an outlet corresponding to the detection area of a sensor of said opto-electric transducer.

4. An apparatus for detecting a circuit pattern comprising: a stage for mounting an object under inspection having a circuit pattern to be detected; means of generating a signal in response to the amount of movement of said stage; a detection optical system for detecting the circuit pattern; an opto-electric transducer which receives the image of the pattern provided by said detection optical system and transforms the image into an image signal; means of calculating the amount of expansion or contraction of the object by detecting the distance between specific patterns on the object; and drive control means which produces a clock signal for said opto-electric transducer based on the stage movement signal provided by said signal generation means and varies the clock signal so as to vary the dimension of the detected image arbitrarily.

5. A circuit pattern detection apparatus according to claim 4 further comprising: means of generating a reference pattern; means of aligning relatively the reference pattern provided by said reference pattern generation means and the image signal provided by said opto-electric transducer; and a judgement means which compares the reference pattern and the detected image signal aligned by said alignment means thereby to detect a defect.

6. An apparatus for detecting a circuit pattern comprising: a stage for mounting an object under inspection having a circuit pattern to be detected; means of generating a signal in response to the amount of movement of said stage; a detection optical system for detecting the circuit pattern; an opto-electric transducer which receives the image of the pattern provided by said detection optical system and transforms the image into an image signal; and drive control means which counts the number of pulses of the stage movement signal provided by said signal generation means, generates a clock signal for said opto-electric transducer when the count has reached a predetermined value, and varies the clock signal so as to vary the dimension of the detected image arbitrarily.

7. An apparatus for generating a reference pattern comprising: means of generating a pattern based on design information which is n times (n is a positive integer) as large as an output image dimension; and means of latching the generated pattern and reading out the latched pattern m times (m is a positive integer) thereby to obtain a reference pattern.

8. A method of detecting a circuit pattern, comprising the steps of:
generating a signal in response to an amount of movement of a stage which mounts an object under inspection having a circuit pattern to be detected;
generating a variable clock signal for an opto-electric transducer, the clock signal being a variable at least in accordance with the generated amount of movement signal; and
receiving by the opto-electric transducer an image of the circuit pattern provided by a detection optical system and producing an image signal thereof in accordance with the variable clock signal.

9. A method according to claim 8, wherein the object under inspection is inspected by comparing the circuit pattern to be detected with a reference pattern.

10. A method according to claim 8, further comprising the steps of:
detecting a distance between specific circuit patterns on the object under inspection;
calculating an amount of expansion or contraction of the object in accordance with the detected distance;
varying the variable clock signal in accordance with the calculated amount; and
utilizing the opto-electric transducer for producing the image signal in accordance with the variable clock signal.

11. A method according to claim 10, wherein the object under inspection is inspected by comparing the circuit pattern to be detected with a reference pattern.

12. A method of detecting a circuit pattern, comprising the steps of:
moving an object under inspection and a sensor relative to one another in steps so that detection areas overlap;
detecting a circuit pattern on the object under inspection with the sensor by varying the amount of step movement;
aligning the detected circuit pattern and a reference circuit pattern; and
inspecting the circuit pattern based upon a comparison of the aligned detected circuit pattern and the reference circuit pattern.

13. A method according to claim 12, wherein the reference circuit pattern is generated based upon design information of the circuit pattern.

14. A method of generating a reference pattern, comprising the steps of:
utilizing design information of a pattern having a predetermined pixel size in relation to a pixel size of a pattern to be inspected;
generating a pattern in accordance with the design information;
latching the generated pattern; and
reading out the latched generated pattern at a predetermined frequency so as to obtain a reference pattern having a pixel size corresponding to the pixel size of the pattern to be inspected.

15. A method according to claim 14, wherein the predetermined pixel size of the pattern of the design information is n times the pixel size of the pattern to be inspected, n being a positive integer greater than 1.

16. A method according to claim 14, wherein the step of latching includes utilizing a line memory for storing the generated pattern, and the step of reading out includes reading out the stored generated pattern from the line memory at the predetermined frequency.

17. An apparatus for generating a reference pattern, comprising:
   means for generating a pattern in accordance with design information of a pattern having a predetermined pixel size in relation to a pixel size of a pattern to be inspected;
   means for latching the generated pattern; and
   means for reading out the latched generated pattern at a predetermined frequency so as to obtain a reference pattern having a pixel size corresponding to the pixel size of the pattern to be inspected.

18. An apparatus according to claim 17, wherein the predetermined pixel size of the pattern of the design information is n times the pixel size of the pattern to be inspected, n being a positive integer greater than 1.

19. An apparatus according to claim 17, wherein the means for latching the generated pattern includes a line memory for storing the generated pattern, and the means for reading out enables reading out of the stored generated pattern from the line memory at the predetermined frequency.

20. An apparatus for generating a reference pattern comprising:
   means for generating a pattern based on design information having a pixel size n times an output image dimension of a desired reference pattern;
   means for latching the generated pattern; and
   means for reading out the latched pattern m times to obtain the reference pattern;
   where n and m are positive integers.

21. An apparatus for generating a two-dimensional reference pattern comprising:
   means for generating a pattern based on design information;
   means for storing the generated pattern in a line memory; and
   means for reading out the stored generated pattern k times from the line memory so as to obtain the reference pattern, where k is a positive integer.

* * * * *